United States Patent
Dubief et al.

(10) Patent No.: US 6,177,090 B1
(45) Date of Patent: Jan. 23, 2001

(54) TOPICAL COMPOSITION CONTAINING A SILICONE-GRAFTED POLYMER AND AN AMINE SILICONE AND/OR A SILICONE GUM OR RESIN

(75) Inventors: Claude Dubief, Le Chesnay; Christine Dupuis; Daniele Cauwet-Martin, both of Paris, all of (FR)

(73) Assignee: L'Oreal, Paris (FR)

(*) Notice: Under 35 U.S.C. 154(b), the term of this patent shall be extended for 0 days.

(21) Appl. No.: 08/983,337

(22) PCT Filed: Sep. 16, 1996

(86) PCT No.: PCT/FR96/01435

§ 371 Date: Dec. 30, 1997

§ 102(e) Date: Dec. 30, 1997

(87) PCT Pub. No.: WO97/12594

PCT Pub. Date: Apr. 10, 1997

(30) Foreign Application Priority Data

Sep. 29, 1995 (FR) .................................................. 95 11481

(51) Int. Cl.[7] ................................. A61K 7/06; A61K 7/48
(52) U.S. Cl. ........................... 424/401; 424/47; 424/70.1; 424/70.2; 424/70.6; 424/70.12; 424/78.02; 514/844; 514/944
(58) Field of Search ................... 424/401, 47, 70.1, 424/70.2, 70.6, 70.12, 78.02; 514/844, 944

(56) References Cited

U.S. PATENT DOCUMENTS

| | | | |
|---|---|---|---|
| 4,587,321 | 5/1986 | Sebag et al. | 528/27 |
| 4,609,750 | 9/1986 | Kollmeier et al. | 556/419 |
| 4,833,225 | 5/1989 | Schaefer et al. | 528/28 |
| 5,104,646 | * 4/1992 | Bolich, Jr. et al. | 424/70 |
| 5,725,882 | * 3/1998 | Kumar et al. | 424/486 |
| 5,837,661 | * 11/1998 | Evans et al. | 510/122 |
| 5,840,291 | * 11/1998 | Tsubakihara et al. | 424/70.12 |
| 6,022,836 | * 2/2000 | Dubief et al. | 510/122 |

FOREIGN PATENT DOCUMENTS

| | | |
|---|---|---|
| 0 017 122 | 10/1980 | (EP) . |
| 0 164 668 | 12/1985 | (EP) . |
| 0 282 720 | 9/1988 | (EP) . |
| 0 530 974 | 3/1993 | (EP) . |
| 0 582 152 | 2/1994 | (EP) . |
| 2 535 730 | 5/1984 | (FR) . |
| WO 89/04161 | 5/1989 | (WO) . |
| WO 92/00303 | 1/1992 | (WO) . |
| WO 93/23009 | 11/1993 | (WO) . |
| WO 95/03776 | 2/1995 | (WO) . |

OTHER PUBLICATIONS

Josef Roidl, Bedeutung der Silicone in der Modernen Kosmetik, Kosmetika, Aerosole, Riechstoffe, vol. 114, No. 2, Feb. 4, 1988, pp. 51–54.*
English Language Derwent Abstract of EP 0 017 122.
Patent Abstracts of Japan, vol. 11, No. 192, Jun. 1987 (JP 62–12712).
Chemical Abstracts, vol. 94, No. 6, Feb. 1981 (Abstract No. 36111s).

* cited by examiner

Primary Examiner—Robert H. Harrison
(74) Attorney, Agent, or Firm—Finnegan, Henderson, Farabow, Garrett & Dunner, L.L.P.

(57) ABSTRACT

A cosmetic or dermatological composition for treating keratinous material, particularly hair, including a cosmetically or dermatologically acceptable medium containing at least one silicone-grafted polymer with a polysiloxane backbone grafted by non-silicone organic monomers and at least one silicone selected from silicones which comprise at least one optionally quaternary amine function, silicone resins, and silicone gums, is disclosed. Such compositions are particularly suitable for use as rinsable or non-rinsable products for washing and conditioning hair, hair setting, or hair styling.

60 Claims, No Drawings

TOPICAL COMPOSITION CONTAINING A SILICONE-GRAFTED POLYMER AND AN AMINE SILICONE AND/OR A SILICONE GUM OR RESIN

This application is a National Stage application under 35 U.S.C. § 371, of International application PCT/FR96/01435, filed Sep. 16, 1996.

The present invention relates to a cosmetic or dermatological composition for treating keratin substances, in particular the hair, comprising at least one grafted silicone polymer containing a polysiloxane skeleton grafted with non-silicone organic monomers, and at least one silicone chosen from silicones containing at least one quaternized or non-quaternized amine function, silicone resins and silicone gums.

Polymers containing a polysiloxane skeleton grafted with non-silicone organic monomers are known in the prior art and are preferably chosen from those described in patent applications EP-A-0,582,152 and WO 93/23009. They are used in particular in hair compositions for their styling properties.

The Applicant has discovered, surprisingly, that by combining at least one silicone polymer containing a polysiloxane skeleton grafted with non-silicone organic monomers, with at least one silicone gum and/or a silicone resin and/or a silicone containing at least one quaternized or non-quaternized amine function, an improvement in the volume and in the body of the hairstyle is obtained while at the same time having better styling and/or holding properties such as the fixing power. The hair is "lighter" and styles easily.

The feel and softness properties of the hair are also improved.

The term fixing power of the composition will be understood to denote the ability of this composition to give the hair cohesion such that the initial shape of the hairstyle is held.

The composition according to the invention is thus essentially characterized in that it comprises, in a cosmetically or dermatologically acceptable medium, at least one grafted silicone polymer containing a polysiloxane skeleton grafted with non-silicone organic monomers, and at least one silicone chosen from silicones containing at least one quaternized or non-quaternized amine function, silicone resins and silicone gums.

In the following text, in accordance with what is generally accepted, the term silicone polymer is understood to denote any organosilicon polymer or oligomer having a linear or cyclic, branched or crosslinked structure, of variable molecular weight, obtained by polymerization and/or polycondensation of suitably functionalized silanes, and consisting essentially of a repetition of main units in which the silicon atoms are linked together by oxygen atoms (siloxane bonding $\equiv$Si—O—Si$\equiv$), optionally substituted hydrocarbon radicals being linked directly via a carbon atom to the said silicon atoms. The most common hydrocarbon radicals are alkyl radicals, especially $C_1$–$C_{10}$ alkyl radicals, and in particular methyl, fluoroalkyl radicals, aryl radicals and in particular phenyl, and alkenyl radicals and in particular vinyl; other types of radicals which can be linked, either directly or via a hydrocarbon radical, to the siloxane chain are, especially, hydrogen, halogens and in particular chlorine, bromine or fluorine, thiols, alkoxy radicals, polyoxyalkylene (or polyether) radicals and in particular polyoxyethylene and/or polyoxypropylene, hydroxyl or hydroxyalkyl radicals, substituted or unsubstituted amine groups, amide groups, acyloxy radicals or acyloxyalkyl radicals, hydroxyalkylamino or aminoalkyl radicals, quaternary ammonium groups, amphoteric or betaine groups, anionic groups such as carboxylates, thioglycolates, sulphosuccinates, thiosulphates, phosphates and sulphates, needless to say this list not being limiting in any way (so-called "organomodified" silicones).

According to the present invention, the grafted silicone polymer(s) which must be used are those which comprise a silicone (or polysiloxane ($\equiv$Si—O—)$_n$) main chain on which is grafted, inside the said chain as well as, optionally, on at least one of its ends, at least one organic group containing no silicone.

These silicone polymers can be existing commercial products or alternatively can be obtained according to any means known to those skilled in the art, in particular by reaction between (i) a starting silicone which is correctly functionalized on one or more of these silicon atoms, and (ii) a non-silicone organic compound which is itself correctly functionalized with a function which is capable of reacting with the functional group(s) borne by the said silicone, forming a covalent bond; a classic example of such a reaction is the hydrosilylation reaction between $\equiv$Si—H groups and vinyl groups $CH_2$=CH—, or alternatively the reaction between thio-functional groups -SH with these same vinyl groups.

Examples of silicone polymers which are suitable for carrying out the present invention, as well as their specific mode of preparation, are described in particular in patent applications EP-A-0,582,152, WO 93/23009 and WO 95/03776, the teachings of which are included in their entirety in the present description by way of non-limiting references.

According to a particularly preferred embodiment of the present invention, the silicone polymer used comprises the result of the radical copolymerization between, on the one hand, at least one non-silicone anionic organic monomer having ethylenic unsaturation and/or a non-silicone hydrophobic organic monomer having ethylenic unsaturation, and, on the other hand, a silicone having in its chain at least one functional group capable of reacting with the said ethylenic unsaturations of the said non-silicone monomers, forming a covalent bond, in particular thio-functional groups.

According to the present invention, the said anionic monomers containing ethylenic unsaturation are preferably chosen, alone or as a mixture, from linear or branched, unsaturated carboxylic acids, optionally partially or totally neutralized in the form of a salt, it being possible for this (these) carboxylic acid(s) to be, more particularly, acrylic acid, methacrylic acid, maleic acid, maleic anhydride, itaconic acid, fumaric acid and crotonic acid. The suitable salts are, in particular, alkali metal salts, alkaline-earth metal salts and ammonium salts. It will likewise be noted that, in the final grafted silicone polymer, the organic group of anionic nature which comprises the result of the radical (homo) polymerization of at least one anionic monomer of unsaturated carboxylic acid type can, after reaction, be post-neutralized with a base (sodium hydroxide, aqueous ammonia, etc) in order to bring it into the form of a salt.

According to the present invention, the hydrophobic monomers containing ethylenic unsaturation are preferably chosen, alone or as a mixture, from acrylic acid esters of alkanols and/or methacrylic acid esters of alkanols. The alkanols are preferably $C_1$–$C_8$ and more particularly $C_1$–$C_{12}$ alkanols. The preferred monomers are chosen from the group consisting of isooctyl (meth)acrylate, isononyl (meth)acrylate, 2-ethylhexyl (meth)acrylate, lauryl (meth)

acrylate, isopentyl (meth)acrylate, n-butyl (meth)acrylate, isobutyl (meth)acrylate, methyl (meth)acrylate, tert-butyl (meth)acrylate, tridecyl (meth)acrylate and stearyl (meth)acrylate, or mixtures thereof.

One family of grafted silicone polymers which is particularly suitable for carrying out the present invention consists of silicone polymers containing in their structure the unit of formula (I) below:

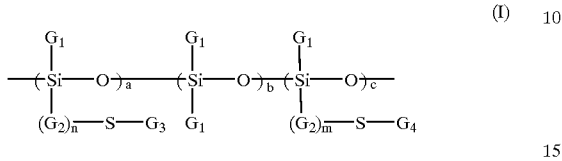
(I)

in which the radicals $G_1$, which may be identical or different, represent hydrogen or a $C_1$—$C_{10}$ alkyl radical or alternatively a phenyl radical; the radicals $G_2$, which may be identical or different, represent a $C_1$—$C_{10}$ alkylene group; $G_3$ represents a polymer residue resulting from the (homo)polymerization of at least one anionic monomer containing ethylenic unsaturation; $G_4$ represents a polymer residue resulting from the (homo)polymerization of at least one hydrophobic monomer containing ethylenic unsaturation; m and n are equal to 0 or 1; a is an integer ranging from 0 to 50; b is an integer which may be between 10 and 350, c is an integer ranging from 0 to 50; with the proviso that one of the parameters a and c is other than 0.

Preferably, the unit of formula (I) above has at least one, and even more preferably all, of the following characteristics:
  the radicals $G_1$ denote an alkyl radical, preferably the methyl radical;
  n is non-zero and the radicals $G_2$ represent a divalent $C_1$—$C_3$ radical, preferably a propylene radical;
  $G_3$ represents a polymeric radical resulting from the (homo)polymerization of at least one monomer of the carboxylic acid type containing ethylenic unsaturation, preferably acrylic acid and/or methacrylic acid;
  $G_4$ represents a polymeric radical resulting from the (homo)polymerization of at least one monomer of the $C_1$—$C_{10}$ alkyl (meth)acrylate type, preferably of the isobutyl or methyl (meth)acrylate type.

Examples of silicone polymers corresponding to formula (I) are, in particular, polydimethylsiloxanes (PDMS) on which are grafted, via a thiopropylene-type connecting chain, mixed polymer units of the poly(meth)acrylic acid type and of the polymethyl (meth)acrylate type.

Other examples of silicone polymers corresponding to formula (I) are, in particular, polydimethylsiloxanes (PDMS) on which are grafted, via a thiopropylene-type connecting chain, polymer units of the polyisobutyl (meth)acrylate type.

Preferably, the number-average molecular mass of the silicone polymers of the invention ranges approximately from 10,000 to 1,000,000, and even more preferably approximately from 10,000 to 100,000.

The grafted silicone polymers in accordance with the invention are preferably used in an amount ranging from 0.01 to 20% by weight relative to the total weight of the composition. More preferably, this amount ranges from 0.1 to 15% by weight and even more particularly from 0.5 to 10% by weight.

Among the silicones containing at least one quaternized or non-quaternized amine function, mention may be made of:

(a) the silicone polymers corresponding to the formula (II) below:

(II)

in which:
$G^1$, $G^2$, $G^3$ and $G^4$, which may be identical or different, denote a hydrogen atom or a phenyl, OH, $C_1$—$C_1$, alkyl, for example methyl, $C_2$—$C_{18}$ alkenyl or $C_1$—$C_{18}$ alkoxy group;
a and a', which may be identical or different, denote the number 0 or an integer from 1 to 3, in particular 0;
b denotes 0 or 1, and in particular 1;
m and n are numbers such that the sum (n+m) can vary especially from 1 to 2000 and in particular from 50 to 150, it being possible for n to denote a number from 0 to 1999 and in particular from 49 to 149 and for m to denote a number from 1 to 2000 and in particular from 1 to 10;
$R^1$, $R^2$, $R^3$ and $R^4$, which may be identical or different, denote a monovalent radical of formula —$C_qH_{2q}O_sR^5_tL$ in which q is a number from 1 to 8, s and t, which may be identical or different, are equal to 0 or 1, $R^5$ denotes an optionally hydroxylated alkylene group and L is an optionally quaternized amine group chosen from the groups:
  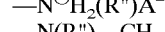
  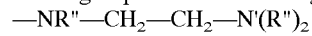
  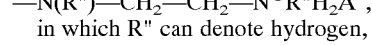
  in which R" can denote hydrogen, phenyl, benzyl or a saturated monovalent hydrocarbon radical, for example an alkyl radical having from 1 to 20 carbon atoms, and $A^-$ represents a halide ion such as, for example, fluoride, chloride, bromide or iodide.

(b) compounds of formula (III):

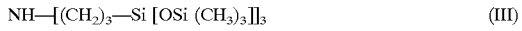
(III)

This compound corresponds to the CTFA name "aminobispropyldimethicone".

Products corresponding to formula (II) are, for example, the polysiloxanes referred to in the CTFA dictionary as "amodimethicone" and corresponding to formula (IV) below:

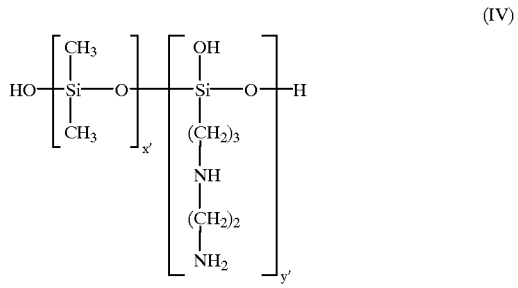
(IV)

in which x' and y' are integers which are dependent on the molecular weight, generally such that the said 5 molecular weight is approximately between 5000 and 20,000.

A product corresponding to formula (II) is the polymer referred to in the CTFA dictionary as "trimethylsilyl amodimethicone", corresponding to the formula (V):

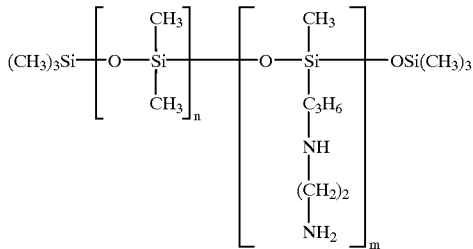
(V)

in which n and m have the meanings given above (cf. formula II).

A commercial product corresponding to this definition is a mixture (90/10 by weight) of a polydimethylsiloxane containing aminoethyl aminoisobutyl groups and of a polydimethylsiloxane sold under the name Q2-8220 by the company Dow Corning.

Such polymers are described, for example, in patent application EP-A-95,238.

Other polymers corresponding to formula (II) are the silicone polymers of the formula:

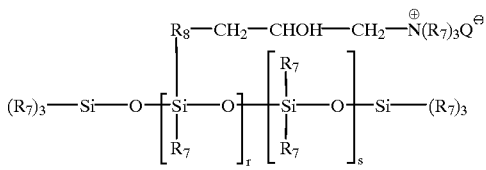

in which:

$R_7$ represents a monovalent hydrocarbon radical having from 1 to 18 carbon atoms, and in particular a $C_1$–$C_{18}$ alkyl or $C_2$–$C_{18}$ alkenyl radical, for example methyl;

$R_8$ represents a divalent hydrocarbon radical, in particular a $C_1$–$C_{18}$ alkylene radical or a divalent $C_1$–$C_{18}$, for example $C_1$–$C_8$, alkyleneoxy radical;

$Q^-$ is a halide ion, in particular chloride;

r represents an average statistical value from 2 to 20 and in particular from 2 to 8;

s represents an average statistical value from 20 to 200 and in particular from 20 to 50.

Such polymers are described more particularly in US Pat. No. 4,185,087.

A polymer corresponding to formula (III) is the polymer sold by the company Union Carbide under the name "Ucar Silicone ALE 56".

When these silicone polymers are used, a particularly advantageous embodiment is their joint use with cationic and/or nonionic surfactants. It is possible to use, for example, the product sold under the name "Emulsion Cationic DC 929" by the company Dow Corning, which comprises, besides amodimethicone, a cationic surfactant comprising a mixture of products corresponding to the formula:

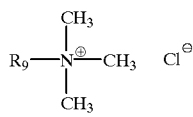

in which $R_9$ denotes alkenyl and/or alkyl radicals having from 14 to 22 carbon atoms, fatty acid derivatives of tallow, in combination with a nonionic surfactant of formula: $C_9H_{19}$—$C_6H_4$—$(OC_2H_4)_{10}$—OH known under the CTFA name "Nonoxynol 10".

Another commercial product which can be used according to the invention is the product sold under the name "Dow Corning Q2 7224" by the company Dow Corning, containing, in combination, the trimethylsilylamodimethicone of formula (V), a nonionic surfactant of formula: $C_8H_{17}$—$C_6H_4$—$(OCH_2CH_2)_n$—OH where n=40, also known as octoxynol-40, another nonionic surfactant of formula: $C_{12}H_25$—$(OCH_2$—$CH_2)_n$—OH where n=6, also known as isolaureth-6, and glycol.

The silicone gums in accordance with the present invention are polydiorganosiloxanes with high molecular masses, of between 200,000 and 2,000,000, used alone or as a mixture in a solvent chosen from volatile silicones, polydimethylsiloxane oils, polymethylphenylsiloxane oils or polydiphenyldimethylsiloxane oils, isoparaffins, methylene chloride, pentane and hydrocarbons, or mixtures thereof.

A silicone gum having a molecular weight of less than 1,500,000 is preferably used. The silicone gums are, for example, a polydimethylsiloxane, a polyphenylmethylsiloxane, a poly(diphenylsiloxane dimethylsiloxane), a poly(dimethylsiloxane methylvinylsiloxane), a poly(dimethylsiloxane phenylmethylsiloxane), a poly(diphenylsiloxane dimethylsiloxane methylvinylsiloxane). These silicone gums can be terminated, at the end of the chain, with trimethylsilyl or dimethylhydroxysilyl groups.

In particular, a silicone gum corresponding to formula (VI):

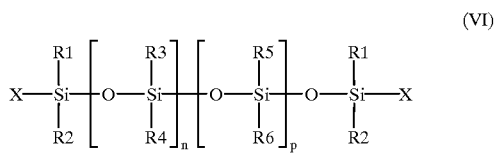
(VI)

in which:

$R_1$, $R_2$, $R_5$ and $R_6$ are, together or separately, an alkyl radical having 1 to 6 carbon atoms, $R_3$ and $R_4$ are, together or separately, an alkyl radical having from 1 to 6 carbon atoms, or an aryl radical, X is an alkyl radical having from 1 to 6 carbon atoms, a hydroxyl radical or a vinyl radical, n and p being chosen so as to give the silicone gum a viscosity of greater than 100,000 mPa.s, preferably greater than 500,000 mPa.s can be used.

In general, n and p can take values from 0 to 5000, preferably from 0 to 3000.

The silicone gum can be introduced into the composition in its natural form or in diluted form in a silicone oil such as a volatile or non-volatile PDMS (polydimethylsiloxane).

As silicone gum which can be used according to the invention, mention may be made of those for which:

the substituents $R_1$ to $R_6$ and X represent a methyl group, p=0 and n=2700, such as that sold under the name SE30 by the company General Electric, the substituents $R_1$ to $R_6$ and X represent a methyl group, p=0 and n=2300, such as that sold under the name AK 500000 by the company Wacker, the substituents $R_1$ to $R_6$ represent a methyl group, the substituent X represents a hydroxyl group, p=0 and n=2700, as a 13% solution in cyclopentasiloxane, such as that sold under the name Q2-1401 by the company Dow Corning, the substituents $R_1$ to $R_6$ represent a methyl group, the substituent X represents a hydroxyl group, p 0 and n=2700, as a 13% solution in dimethicone, such as that sold under the name Q2-1403 by the company Dow Corning, the substituents $R_1$, $R_2$, $R_5$, $R_6$ and X represent a methyl group, the substituents $R_3$ and $R_4$ represent an aryl group such that the molecular weight of the compound is 600,000, such as that sold under the name 761 by the company Rhône-Poulenc.

The silicone resins which can be used in accordance with the invention are crosslinked siloxane systems containing the units: $R_2SiO_{2/2}$, $RSiO_{3/2}$ and $SiO_{4/2}$ in which R represents a hydrocarbon group having from 1 to 6 carbon atoms or a phenyl group. Among these products, those particularly preferred are those in which R denotes a lower alkyl radical ($C_1$–$C_6$) or a phenyl radical.

Among these resins, mention may be made of the product sold under the name "Dow Corning 593" or those sold under the names "Silicone Fluid SS 4230" and "SS 4267" by the company General Electric and which are "dimethyl/trimethylpolysiloxanes".

The silicone gums or resins and/or the amino silicones are preferably used in an amount of between 0.01 and 50% by weight relative to the total weight of the composition, preferably between 0.05 and 20% by weight. Even more preferably, this amount is between 0.1 and 10% by weight.

The cosmetically or dermatologically acceptable medium preferably consists of water or a mixture of water and cosmetically acceptable solvents such as monoalcohols, polyalcohols, glycol ethers or fatty acid esters, which can be used alone or as a mixture.

Mention may be made more particularly of lower alcohols such as ethanol and isopropanol, polyalcohols such as diethylene glycol, glycol ethers, glycol alkyl ethers or diethylene glycol alkyl ethers.

The grafted silicone polymers according to the invention can be dissolved in the said cosmetically acceptable medium or used in the form of an aqueous dispersion of particles.

The composition of the invention can also contain at least one additive chosen from thickeners, fatty acid esters, fatty acid esters of glycerol, volatile silicones, surfactants, fragrances, preserving agents, sunscreens, proteins, vitamins, polymers, plant, animal, mineral or synthetic oils or any other additive conventionally used in the cosmetics field.

These additives are present in the composition according to the invention in proportions which can range from 0 to 20% by weight relative to the total weight of the composition. The precise amount of each additive depends on its nature and is determined readily by those skilled in the art.

Needless to say, a person skilled in the art will take care to select the optional compound(s) to be added to the composition according to the invention such that the advantageous properties intrinsically associated with the composition in accordance with the invention are not, or are not substantially, adversely affected by the addition envisaged.

The compositions according to the invention can be in the form of a gel, a milk, a cream, a relatively thickened lotion or a mousse.

The compositions according to the invention are used as rinse-out products or as leave-in products in particular to wash, care for, condition, maintain the style of or shape keratin substances such as the hair.

These compositions are more particularly styling products such as hairsetting lotions, blow-drying lotions, fixing compositions (lacquers) and styling compositions. The lotions can be packaged in various forms, in particular in vaporizers, pump-dispenser bottles or in aerosol containers in order to ensure application of the composition in vaporized form or in the form of a mousse. Such packaging forms are indicated, for example, when it is desired to obtain a spray, a lacquer or a mousse for fixing or treating the hair.

The compositions can also be shampoos, rinse-out or leave-in compositions, to be applied before or after shampooing, dyeing, bleaching, permanent-waving or straightening the hair.

When the composition according to the invention is packaged in aerosol form in order to obtain a lacquer or an aerosol mousse, it comprises at least one propellant which can be chosen from volatile hydrocarbons such as n-butane, propane, isobutane, pentane, a chloro and/or fluoro hydrocarbon, and mixtures thereof. Carbon dioxide, nitrous oxide, dimethyl ether, nitrogen or air, which is compressed, and mixtures thereof, can also be used as propellant.

Another subject of the invention is a process for treating keratin substances such as the hair, which consists in applying a composition as defined above to the hair and then optionally in rinsing with water.

The invention will now be illustrated more fully with the aid of the examples which follow, which should not be considered as limiting it to the embodiments described. In the text which follows, AM means active material.

EXAMPLE 1

A shampoo having the following composition was prepared:

| | |
|---|---|
| Sodium lauryl ($C_{12}/C_{14}$ 70/30) ether sulphate oxyethylenated with 2.2 mol of ethylene oxide, as an aqueous solution containing 28% AM, sold under the name Empicol ESB 31/F by the company Albright and Wilson | 14 g AM |
| Cocoylbetaine as an aqueous solution containing 28% AM | 3 g AM |
| Grafted silicone polymer of formula (I) of polymethyl/methylsiloxane structure containing 3-propylthio polyisobutyl methacrylate groups in solution in a cyclic volatile silicone | 1 g |
| Mixture (47/53 by weight) of 1-(hexadecyl-oxy)-2-octadecanol and cetyl alcohol | 2 g |
| Coconut acid monoisopropanolamide | 2 g |
| Polydimethylsiloxane containing amino-ethyl aminopropyl groups as a cationic 35% emulsion in water, sold by Dow Corning under the name DC 939 | 1 g AM |
| Fragrance, sequestering agent, preserving agent | |
| Water | q.s. 100 g |

The pH is adjusted to 5 by addition of sodium hydroxide.

EXAMPLE 2

A rinse-out conditioner of the following composition was prepared:

| | |
|---|---|
| Grafted silicone polymer of formula (I) of polymethyl/methylsiloxane structure containing 3-propylthio polyisobutyl methacrylate groups in solution in a cyclic volatile silicone | 2 g |
| Crosslinked copolymer of trimethylethyl-ammonium methacrylate chloride and of acrylamide (42/58 by weight), sold as a dispersion in oil containing 50% AM by the company Allied Colloids under the name Salcare SC 92 | 1 g AM |
| Mixture (56/44 by weight) of an α, Ω-dihydroxy polydimethylsiloxane and of volatile cyclic silicones, sold uner the name Q2-1401 by the company Dow Corning | 2 g |
| Fragrance, preserving agent | |
| Water | q.s. 100 g |

The pH is adjusted to 7 by addition of sodium hydroxide.

What is claimed is:

1. A cosmetic or dermatological composition comprising, in a cosmetically or dermatologically acceptable medium, (a) at least one grafted silicone polymer containing a polysiloxane skeleton grafted with at least one non-silicone organic monomer, and (b) at least one silicone selected from silicones containing at least one optionally quaternized amine function, silicone resins and silicone gums, wherein said at least one silicone is different from said at least one grafted silicone polymer.

2. A cosmetic or dermatological composition according to claim 1, wherein said cosmetic or dermatological composition is a treatment composition for a keratin substance.

3. A cosmetic or dermatological composition according to claim 2, wherein said keratin substance is human hair.

4. A cosmetic or dermatological composition according to claim 1, wherein said at least one grafted silicone polymer comprises a polysiloxane skeleton on which is grafted, inside said skeleton as well as, optionally, on at least one of its ends, said at least one non-silicone organic monomer.

5. A cosmetic or dermatological composition according to claim 1, wherein said at least one grafted silicone polymer is obtained by radical copolymerization between:

at least one non-silicone organic monomer having ethylenic unsaturation selected from anionic and hydrophobic monomers, and at least one polysiloxane having in its skeleton at least one functional group capable of reacting with said ethylenic unsaturation of said non-silicone monomer.

6. A cosmetic or dermatological composition according to claim 5, wherein said at least one polysiloxane has several functional groups capable of reacting with said ethylenic unsaturation of said at least one non-silicone monomer.

7. A cosmetic or dermatological composition according to claim 5, wherein said at least one non-silicone anionic organic monomer is selected from linear or branched, unsaturated carboxylic acids, optionally partially or totally neutralized in the form of a salt.

8. A cosmetic or dermatological composition according to claim 7, wherein said at least one non-silicone anionic organic monomer is selected from acrylic acid, methacrylic acid, maleic acid, maleic anhydride, itaconic acid, fumaric acid and crotonic acid, alkali metal salts of said acids, alkaline-earth metal salts of said acids and ammonium salts of said acids.

9. A cosmetic or dermatological composition according to claim 5, wherein said at least one hydrophobic organic monomer is selected from acrylic acid esters of alkanol and methacrylic acid esters of alkanol.

10. A cosmetic or dermatological composition according to claim 9, wherein said alkanol is selected from $C_1$–$C_{18}$ alkanols.

11. A cosmetic or dermatological composition according to claim 10, wherein said alkanol is selected from $C_1$–$C_{12}$ alkanols.

12. A cosmetic or dermatological composition according to claim 5, wherein said at least one hydrophobic organic monomer is selected from isooctyl (meth)acrylate, isononyl (meth)acrylate, 2-ethylhexyl (meth)acrylate, lauryl (meth)acrylate, isopentyl (meth)acrylate, n-butyl (meth)acrylate, isobutyl (meth)acrylate, methyl (meth)acrylate, tert-butyl (meth)acrylate, tridecyl (meth)acrylate and stearyl (meth)acrylate.

13. A cosmetic or dermatological composition according to claim 1, wherein said at least one grafted silicone polymer comprises, on the main silicone chain, at least one non-silicone anionic organic group obtained by radical (homo)polymerization of at least one non-silicone anionic monomer of unsaturated carboxylic acid, partially or totally neutralized in the form of a salt.

14. A cosmetic or dermatological composition according to claim 5, wherein said at least one grafted silicone polymer is selected from silicone polymers containing in their structure the unit of formula (I):

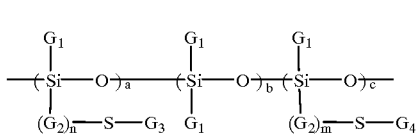

in which:

radicals G, independently represent hydrogen or a $C_1$–$C_{10}$ alkyl radical or a phenyl radical;

radicals $G_2$ independently represent a divalent $C_1$–$C_{10}$ alkylene group;

$G_3$ represents a polymer residue resulting from the (homo)polymerization of at least one anionic monomer containing ethylenic unsaturation;

$G_4$ represents a polymer residue resulting from the (homo)polymerization of at least one hydrophobic monomer containing ethylenic unsaturation;

m and n are equal to 0 or 1;

a is an integer ranging from 0 to 50;

b is an integer ranging from 10 to 350;

c is an integer ranging from 0 to 50;

with the proviso that one of the parameters a and c is not 0.

15. A cosmetic or dermatological composition according to claim 14, wherein said unit of formula (I) has at least one of the following characteristics:

said radicals $G_1$ denote a C–$C_{10}$ alkyl radical;

n is 1 and said radicals $G_2$ represent a divalent $C_1$–$C_3$ radical;

$G_3$ represents a polymeric residue resulting from the (homo)polymerization of at least one monomer of the carboxylic acid type containing ethylenic unsaturation;

G$_4$ represents a polymeric residue resulting from the (homo)polymerization of at least one monomer of the C$_1$–C$_{10}$ alkyl (meth)acrylate type.

16. A cosmetic or dermatological composition according to claim 14, wherein said unit of formula (I) simultaneously has the following characteristics:
said radicals G$_1$ denote a methyl radical;
n is 1 and said radicals G$_2$ represent a propylene radical;
G$_3$ represents a polymeric residue resulting from the (homo)polymerization of at least one monomer selected from acrylic acid and methacrylic acid;
G$_4$ represents a polymeric residue resulting from the (homo)polymerization of at least one monomer selected from isobutyl and methyl (meth)acrylate monomers.

17. A cosmetic or dermatological composition according to claim 1, wherein said at least one grafted silicone polymer has a number-average molecular mass ranging from 10,000 to 1,000,000.

18. A cosmetic or dermatological composition according to claim 17, wherein said at least one grafted silicone polymer has a number-average molecular mass ranging from 10,000 to 100,000.

19. A cosmetic or dermatological composition according to claim 1, wherein said at least one grafted silicone polymer is present in a concentration ranging from 0.01 to 20% by weight relative to the total weight of said composition.

20. A cosmetic or dermatological composition according to claim 14, wherein said at least one grafted silicone polymer is present in a concentration ranging from 0.1 to 15% by weight relative to the total weight of said composition.

21. A cosmetic or dermatological composition according to claim 20 wherein said at least one grafted silicone polymer is present in a concentration ranging from 0.5 to 10% by weight relative to the total weight of said composition.

22. A cosmetic or dermatological composition according to claim 1, wherein said at least one silicone selected from silicones containing at least one optionally quaternized amine function, silicone resins and silicone gums, is present in a concentration ranging from 0.01 to 50% by weight relative to the total weight of said composition.

23. A cosmetic or dermatological composition according to claim 22, wherein said at least one silicone is present in a concentration ranging from 0.05 to 20% by weight relative to the total weight of said composition.

24. A cosmetic or dermatological composition according to claim 23, wherein said at least one silicone is present in a concentration ranging from 0.1 to 10% by weight relative to the total weight of said composition.

25. A cosmetic or dermatological composition according to claim 1, wherein said at least one silicone containing at least one optionally quaternized amine function is selected from:

(a) silicone polymers corresponding to formula (II):

$$R^1{}_a G^1{}_{3-a}-Si(OSiG^2{}_2)_n-(OSiG^3{}_b R^2{}_{2-b})_m-O-SiG^4{}_{3-a'}-R^3{}_{a'} \quad (II)$$

in which:
G$^1$, G$^2$, G$^3$ and G$^4$ independently denote a hydrogen atom or a phenyl, OH, C$_1$–C$_{10}$ alkyl, C$_2$–C$_{18}$ alkenyl or C$_1$–C$_{18}$ alkoxy group;
a and a' independently denote the number 0 or an integer from 1 to 3;
b denotes 0 or 1;
wherein the sum (n+m) ranges from 1 to 2000, it being possible for n to denote a number ranging from 0 to 1999 and for m to denote a number ranging from 1 to 2000;

R$^1$, R$^2$ and R$^3$ independently denote a monovalent radical of formula —C$_q$H$_{2q}$O$_s$R$^5{}_t$L, wherein
q is a number ranging from 1 to 8;
s and t independently are equal to 0 or 1;
R$^5$ denotes an optionally hydroxylated alkylene group; and
L is an optionally quaternized amine group selected from:
—NR"—CH$_2$—CH$_2$—N'(R")$_2$,
—N(R")$_2$,
—N$^\ominus$(R")$_3$A$^-$,
—N$^\ominus$H(R")$_2$A$^-$,
—N$^\ominus$H$_2$(R")A$^-$, and
—N(R")—CH$_2$—CH$_2$—N$^\ominus$R"H$_2$A$^-$,
in which
R" independently denotes hydrogen, phenyl, benzyl or a saturated
monovalent hydrocarbon radical; and
A$^-$ represents a halide ion and (b) compounds of formula (III) below:

NH—[(CH$_2$)$_3$—Si[OSi(CH$_3$)$_3$]]$_3$      (III).

26. A cosmetic or dermatological composition according to claim 25, wherein, with respect to G$^1$, G$^2$, G$^3$ and G$^4$, said C$_1$–C$_{18}$ alkyl is methyl.

27. A cosmetic or dermatological composition according to claim 25, wherein a and a' independently denotes 0.

28. A cosmetic or dermatological composition according to claim 25, wherein b denotes 1.

29. A cosmetic or dermatological composition according to claim 25, wherein the sum (n+m) ranges from 50 to 150; n ranges from 49 to 149; and m ranges from 1 to 10.

30. A cosmetic or dermatological composition according to claim 25, wherein R" denotes an alkyl radical having from 1 to 20 carbon atoms.

31. A cosmetic or dermatological composition according to claim 25, wherein A$^-$ represents a halide ion selected from fluoride, chloride, bromide or iodide.

32. A cosmetic or dermatological composition according to claim 25, wherein said silicone polymers corresponding to formula (II) are selected from:

(a) polysiloxanes corresponding to formula (IV):

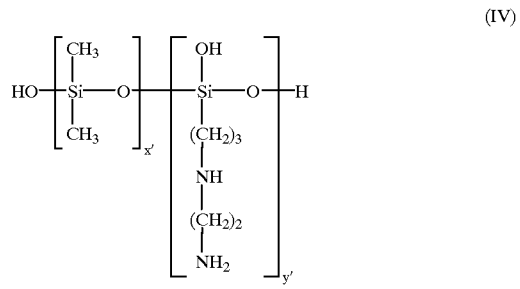

in which:
x' and y' are integers which are dependent on the molecular weight of said polysiloxanes of formula (IV)

(b) polymers corresponding to formula (V):

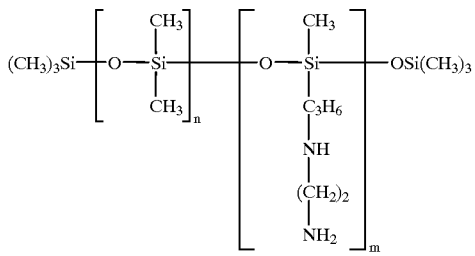

(V)

in which:
the sum (n+m) ranges from 1 to 2000, it being possible for n to denote a number ranging from 0 to 1999 and for m to denote a number ranging from 1 to 2000; and (c) silicone polymers corresponding to the formula:

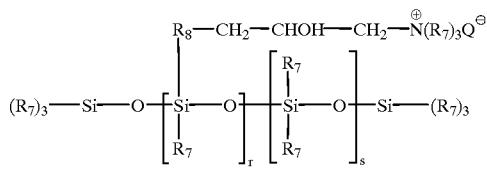

in which:
$R_7$ represents a monovalent hydrocarbon radical having from 1 to 18 carbon atoms;
$R_8$ represents a divalent hydrocarbon radical;
$Q^-$ is a halide ion;
r represents an average statistical value from 2 to 20; and
s represents an average statistical value from 20 to 200.

33. A cosmetic or dermatological composition according to claim 32, wherein x' and y' are such that the molecular weight of the polysiloxanes corresponding to formula (IV) ranges from 5000 to 20,000.

34. A cosmetic or dermatological composition according to claim 32, wherein the sum (n+m) ranges from 50 to 150; n ranges from 49 to 149; and m ranges from 1 to 10.

35. A cosmetic or dermatological composition according to claim 32, wherein $R_7$ represents a $C_1$–$C_{18}$ alkyl or $C_2$–$C_{18}$ alkenyl radical.

36. A cosmetic or dermatological composition according to claim 35, wherein $R_7$ represents methyl.

37. A cosmetic or dermatological composition according to claim 32, wherein $R_8$ represents a divalent $C_1$–$C_{18}$ alkylene radical or a divalent $C_1$–$C_{18}$ alkyleneoxy radical.

38. A cosmetic or dermatological composition according to claim 37, wherein $R_8$ represents a divalent $C_1$–$C_8$ alkyleneoxy radical.

39. A cosmetic or dermatological composition according to claim 32, wherein $Q^-$ is chloride.

40. A cosmetic or dermatological composition according to claim 32, wherein r represents an average statistical value ranging from 2 to 8.

41. A cosmetic or dermatological composition according to claim 32, wherein s represents an average statistical value ranging from 20 to 50.

42. A cosmetic or dermatological composition according to claim 1, wherein said silicone gums are polydiorganosiloxanes with molecular masses ranging from 200,000 to 2,000,000.

43. A cosmetic or dermatological composition according to claim 42, wherein said molecular masses are less than 1,500,000.

44. A cosmetic or dermatological composition according to claim 42, wherein said silicone gums are present alone or as a mixture with at least one solvent selected from volatile silicones, polydimethylsiloxane oils, polymethylphenylsiloxane oils, polydiphenyldimethylsiloxane oils, isoparaffins, methylene chloride, pentane and hydrocarbons.

45. A cosmetic or dermatological composition according to claim 42, wherein said polydiorganosiloxanes are selected from polydimethylsiloxane, polyphenylmethylsiloxane, poly(diphenylsiloxane dimethylsiloxane), poly(dimethylsiloxane methylvinylsiloxane), poly(dimethylsiloxane phenylmethylsiloxane), and poly(diphenylsiloxane dimethylsiloxane methylvinylsiloxane).

46. A cosmetic or dermatological composition according to claim 1, wherein said silicone gums correspond to formula (VI):

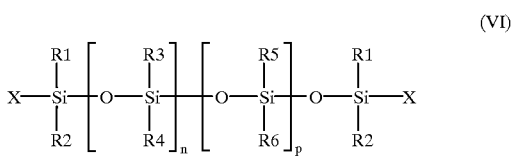

(VI)

in which:
$R_1$, $R_2$, $R_5$ and $R_6$ are, together or separately, an alkyl radical having 1 to 6 carbon atoms,
$R_3$ and $R_4$ are, together or separately, an alkyl radical having from 1 to 6 carbon atoms, or an aryl radical,
X is an alkyl radical having from 1 to 6 carbon atoms, a hydroxyl radical or a vinyl radical, and
n and p are selected so as to give the silicone gum a viscosity of greater than 100,000 mPa.s.

47. A cosmetic or dermatological composition according to claim 46, wherein said viscosity is greater than 500,000 mPa.s.

48. A cosmetic or dermatological composition according to claim 46, wherein n and p have values ranging from 0 to 5000.

49. A cosmetic or dermatological composition according to claim 48, wherein n and p have values ranging form 0 to 3000.

50. A cosmetic or dermatological composition according to claim 1, wherein said composition further comprises at least one additive selected from thickeners, fatty acid esters, fatty acid esters of glycerol, silicones, surfactants, fragrances, preserving agents, sunscreens, proteins, vitamins, different polymers, plant, animal, mineral and synthetic oils and any other suitable cosmetic additive.

51. A cosmetic or dermatological composition according to claim 1, wherein said cosmetically or dermatologically acceptable medium comprises water or a mixture of water and at least one cosmetically acceptable solvent.

52. A cosmetic or dermatological composition according to claim 51, wherein said at least one cosmetically acceptable solvent is selected from monoalcohols, polyalcohols, glycol ethers and fatty acid esters.

53. A cosmetic or dermatological composition according to claim 1, wherein said composition is in the form of a gel, a milk, a cream, a thickened lotion or a mousse.

54. A cosmetic or dermatological composition according to claim 1, wherein said composition is a hair product.

55. A cosmetic or dermatological composition according to claim 54, wherein said hair product is selected from shampoos and rinse-out and leave-in hair products, to be applied before or after shampooing, dyeing, bleaching, permanent-waving or straightening the hair.

56. A cosmetic or dermatological composition according to claim 1, wherein said composition is packaged in the form of a vaporizer, a pump-dispenser bottle or an aerosol container.

57. A cosmetic or dermatological composition according to claim 1, wherein said at least one grafted silicone polymer is dissolved in the cosmetically or dermatologically acceptable medium or is in the form of an aqueous dispersion of particles.

58. A non-therapeutic process for treating a keratin substance comprising applying at least one composition according to claim 1 to said keratin substance and then optionally rinsing with water.

59. A non-therapeutic process according to claim 58, wherein said keratin substance is human hair.

60. A cosmetic or dermatological composition comprising, in a cosmetically or dermatologically acceptable medium,
   (a) at least one grafted silicone polymer containing a polysiloxane skeleton grafted with at least one non-silicone organic monomer,
   (b) at least one silicone selected from silicone resins and silicone gums, wherein said at least one silicone is different from said at least one grafted silicone polymer, and
   (c) optionally, a silicone containing at least one optionally quaternized amine function.

* * * * *

UNITED STATES PATENT AND TRADEMARK OFFICE
CERTIFICATE OF CORRECTION

PATENT NO.: 6,177,090 B1

DATED: January 23, 2001

INVENTOR(S): Claude DUBIEF et al.

It is certified that errors appear in the above-identified patent and that said Letters Patent is hereby corrected as shown below:

Front page, line 2, change "Daniele" to "Danièle".
Claim 14, column 10, line 43, change "G," to -- $G_1$ --.
Claim 14, column 10, line 53, change "0or 1" to -- 0 or 1 --.
Claim 14, column 10, line 55, change "10to 350" to -- 10 to 350 --.
Claim 15, column 10, line 62, change "C-$C_{10}$" to -- $C_1$-$C_{10}$ --.
Claim 20, column 11, line 28, change "claim 14" to -- claim 5 --.
Claim 38, column 13, line 54, change "diva lent" to -- divalent --.
Claim 40, column 13, line 59, change "a n" to -- an --.

Signed and Sealed this

Fifteenth Day of May, 2001

Attest:

NICHOLAS P. GODICI

Attesting Officer    Acting Director of the United States Patent and Trademark Office